(12) United States Patent
Gaussa et al.

(10) Patent No.: US 9,901,691 B2
(45) Date of Patent: Feb. 27, 2018

(54) EXSUFFLATION SYNCHRONIZATION (75) Inventors: William Gaussa, Eindhoven (NL);
Maarten Leonardus Christian Brand, Eindhoven (NL); Peter Hill, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 855 days.

(21) Appl. No.: 13/993,195

(22) PCT Filed: Dec. 1, 2011

(86) PCT No.: PCT/IB2011/055414
§ 371 (c)(1),
(2), (4) Date: Jun. 11, 2013

(87) PCT Pub. No.: WO2012/080892
PCT Pub. Date: Jun. 21, 2012

(65) Prior Publication Data
US 2013/0269699 A1    Oct. 17, 2013

Related U.S. Application Data (60) Provisional application No. 61/422,244, filed on Dec. 13, 2010.

(51) Int. Cl.
*A61M 16/00* (2006.01)
*A61H 31/00* (2006.01)
(Continued)

(52) U.S. Cl.
CPC ........ *A61M 16/0057* (2013.01); *A61M 16/00* (2013.01); *A61M 16/0009* (2014.02);
(Continued)

(58) Field of Classification Search
CPC .......... A61M 16/0057; A61M 16/0009; A61M 2205/52; A61M 2205/3592;
(Continued)

(56) References Cited

U.S. PATENT DOCUMENTS 6,030,353 A * 2/2000 Van Brunt ........... A61H 9/0078
239/431
6,439,229 B1 * 8/2002 Du ........................ A61M 16/00
128/204.21
(Continued)

FOREIGN PATENT DOCUMENTS

JP    2007512905 A    5/2007
JP    2009507609 A    2/2009
(Continued)

OTHER PUBLICATIONS

Bach, J.R. "Mechanical insufflation-exsufflation. Comparison of peak expiratory flows with manually assisted and unassisted coughing techniques." Chest (1993) 104:1553-1562.*
(Continued)

*Primary Examiner* — Valerie L Woodward
*Assistant Examiner* — Douglas Sul
(74) *Attorney, Agent, or Firm* — Michael W. Haas (57) ABSTRACT

Systems and methods for synchronizing machine-induced expiratory airflow of a subject with user-induced expiratory airflow include an indicator time at which a user should initiate treatment to aid airway clearance of the subject. Such treatment may include compressing the stomach area of the subject. At the indicator time, a user responds to an indication, e.g. an audible sound, by initiating treatment in accordance with a therapeutic regimen.

15 Claims, 5 Drawing Sheets

(51) Int. Cl.
    *A61M 16/06* (2006.01)
    *A61M 16/08* (2006.01)
(52) U.S. Cl.
    CPC .... *A61M 16/0666* (2013.01); *A61M 16/0875* (2013.01); *A61H 31/00* (2013.01); *A61H 2201/5007* (2013.01); *A61H 2201/5023* (2013.01); *A61H 2205/083* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/583* (2013.01)
(58) Field of Classification Search
    CPC .... A61H 2201/5023; A61H 2201/5007; A61H 2205/083
    See application file for complete search history.

(56) References Cited

U.S. PATENT DOCUMENTS

| | | | | |
|---|---|---|---|---|
| 7,096,866 | B2* | 8/2006 | Be'eri | A61M 16/20 128/205.19 |
| 8,460,223 | B2* | 6/2013 | Huster | A61M 16/00 601/149 |
| 2005/0039749 | A1 | 2/2005 | Emerson | |
| 2007/0060785 | A1 | 3/2007 | Freeman | |
| 2007/0199566 | A1* | 8/2007 | Be'eri | A61M 16/0051 128/204.23 |
| 2010/0122699 | A1* | 5/2010 | Birnkrant | A61M 1/0023 128/204.21 |
| 2010/0160839 | A1* | 6/2010 | Freeman | A61H 31/00 601/41 |
| 2011/0220107 | A1* | 9/2011 | Kimm | A61M 16/00 128/204.21 |

FOREIGN PATENT DOCUMENTS

| | | |
|---|---|---|
| JP | 2009509610 A | 3/2009 |
| WO | WO2005056076 A2 | 6/2006 |
| WO | WO2007054829 A2 | 5/2007 |
| WO | WO2010106451 A1 | 9/2010 |
| WO | WO2012042255 A1 | 4/2012 |

OTHER PUBLICATIONS

Sivasothy et al, "Effect of manually assisted cough and mechanical insufflation on cough flow of normal subjects, patients with chronic obstructive pulmonary disorder (COPD), and patients with respiratory muscle weakness," Thorax 2001; 56:438-444.*

* cited by examiner

EXSUFFLATION SYNCHRONIZATION

This patent application claims the priority benefit under 35 U.S.C § 371 of international patent application no. PCT/IB2011/055414, filed Dec. 1, 2011, which claims the priority benefit under 35 U.S.C. § 119(e) of U.S. Provisional Application No. 61/422,244 filed on Dec. 13, 2010, the contents of which are herein incorporated by reference.

BACKGROUND OF THE INVENTION

1. Field of the Invention

The invention relates to synchronizing the operation of a mechanical insufflation/exsufflation system with user-induced and/or manually-induced exsufflation for patients undergoing airway pressure therapy.

2. Description of the Related Art

Patients (or subjects) may undergo airway pressure therapy by mechanical insufflation/exsufflation, e.g. to enhance lung mucus clearance. The exsufflation phase may create airflow in the respiratory system of a subject that simulates a cough. The subject may benefit if a caretaker (or user) would enhance cough clearance by manually compressing the stomach area of the subject at the right moment or by applying another treatment to aid airway clearance.

SUMMARY OF THE INVENTION

Accordingly, it is an object of the present invention to provide an insufflation/exsufflation therapy and system for providing same that overcomes the shortcomings of conventional techniques. This object is achieved according to one embodiment of the present invention by providing a methods for synchronizing machine-induced expiratory airflow of a subject with user-induced expiratory airflow of the subject.

Subjects using mechanical insufflation/exsufflation may need assistance with lung mucus clearance, a.k.a. airway clearance or cough clearance. Mechanical exsufflation may create airflow in the airway of a subject that simulates a cough and thus aids airway clearance. Mechanical exsufflation may be achieved by first generating, by a pressure generator, a pressurized flow of breathable gas for delivery to the airway of the subject at a first pressure level, and then reducing the pressure of the pressurized flow of breathable gas to a second pressure level that is less than the first pressure level, the reduction corresponding to a transition time that is determined in accordance with a therapeutic respiratory regimen. The first pressure level may be a positive pressure level, and the second pressure level may be a negative pressure level. Operation of the pressure generator may be controlled by a control module which is an executable computer program module. Transition times for a naturally occurring unaided cough for a typical human subject may be shorter than a second. Synchronization of machine-induced (i.e. mechanical) exsufflation with user-induced exsufflation—e.g. manual exsufflation by compression the stomach area of a subject—may include determining an indicator time at which an indication should be conveyed to the user indicating that the user should initiate treatment to aid airway clearance of the subject. The indicator time and the transition time may be determined by a timing module which is an executable computer program module. At the indicator time the indication may be conveyed to the user via a user interface under control of an interface module, which is an executable computer program module.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

DETAILED DESCRIPTION OF THE EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
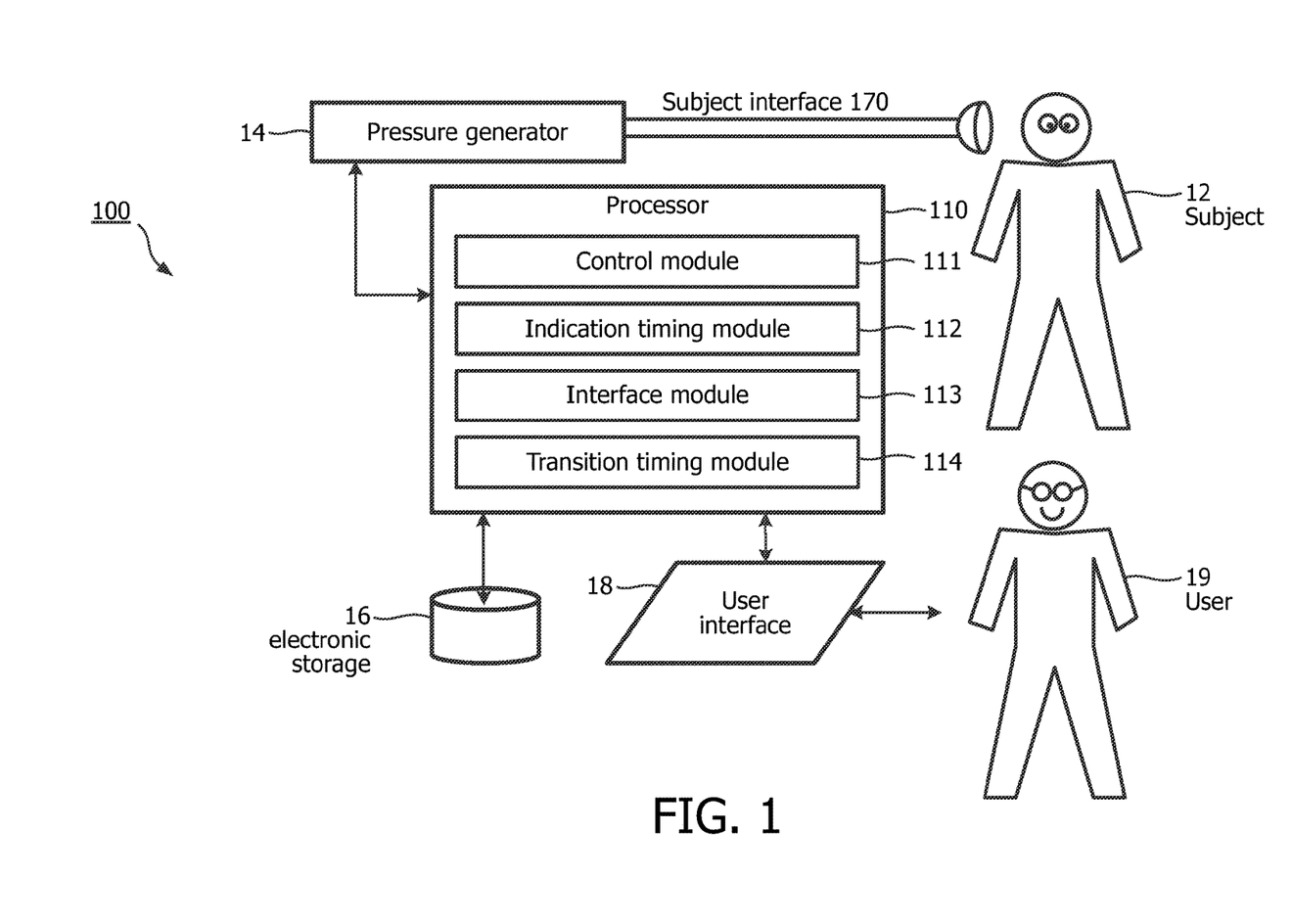
FIG. 1 illustrates an exemplary implementation of an exsufflation synchronization system, a subject, and a user.

FIG. 1 illustrates an exemplary implementation of an exsufflation synchronization system 100, a subject 12, and a user 19. System 100 may be configured to deliver a pressurized flow of breathable gas to the airway of a subject 12 in accordance with a therapy regime. The pressurized flow of breathable gas may be delivered to the airway of subject 12 while the subject sleeps. System 100 may be further configured to monitor the respiration of subject 12. In one embodiment, system 100 includes one or more of a pressure generator 14, a user interface 18, subject interface 170, electronic storage 16, processor 110, and/or other components.

In one embodiment, pressure generator 14 is configured to generate a pressurized flow of breathable gas for delivery to the airway of subject 12 via subject interface 170. Pressure generator 14 may control one or more parameters of the pressurized flow of breathable gas, including pressure, flow rate, temperature, humidity, velocity, acceleration, gas composition, acoustics, changes in a parameter indicative of respiration, gas parameters, and/or other parameters for therapeutic purposes, or for other purposes. By way of non-limiting example, pressure generator 14 may be part of a mechanical insufflation/exsufflation appliance configured to control the pressure of a pressurized flow of breathable gas to provide pressure support to the airway of subject 12. Examples of such an appliance may be a CPAP appliance, an ASV appliance, and/or other appliances. As such, the appliance may include a pressure generator, a respiratory circuit, and/or other components.

The respiratory circuit, e.g. subject interface 170, may be configured to deliver the pressurized flow of breathable gas from pressure generator 14 to the airway of subject 12. The respiratory circuit may include a conduit and a subject interface appliance. The conduit may place the subject interface appliance in fluid communication with the pressure generator.

The pressurized flow of breathable gas is delivered to the airway of subject 12 via subject interface 170, which is configured to communicate the pressurized flow of breathable gas generated by pressure generator 14 to the airway of subject 12. The subject interface appliance may be invasive or non-invasive. The subject interface appliance may include, for example, a nasal cannula, a nasal mask, a nasal/oral mask, a full face mask, a total face mask, air outlet, or other interface appliances that communication a flow of gas with an airway of a subject, and/or other appliances. The present invention is not limited to these examples, and contemplates delivery of the pressurized flow of breathable gas to subject 12 using any physical subject interface.

Pressure generator 14 may include a positive pressure generator and/or a negative pressure generator. Pressure generator 14 may generate the pressurized flow of breathable gas to mechanically ventilate subject 12. Pressure generator 14 may control the pressure of the pressurized flow of breathable gas to mechanically inflate and deflate the lungs to facilitate gas exchange within the lungs.

In one embodiment, electronic storage 16 comprises electronic storage media that electronically stores information. The electronic storage media of electronic storage 16 may include one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 110, information received via user interface 18, and/or other information that enables system 100 to function properly. Electronic storage 16 may be (in whole or in part) a separate component within system 100, or electronic storage 16 may be provided (in whole or in part) integrally with one or more other components of system 100 (e.g., generator 14, user interface 18, processor 110, etc.).

User interface 18 is configured to provide an interface between system 100 and one or more users (e.g., user 19, a caregiver, a doctor, a researcher, a therapy decision-maker, etc.) through which the users may provide information to and receive information from system 100. This enables data, cues, results, and/or instructions and any other communicable items, collectively referred to as "information," to be communicated between the users and one or more of pressure generator 14, electronic storage 16, and/or processor 110. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 18 include, but are not limited to, an RS-232 port, RF link, an IR link, modem (telephone, cable or other). In short, any technique for communicating information with system 100 is contemplated by the present invention as user interface 18.

Processor 110 is configured to provide information processing capabilities in system 100. As such, processor 110 may include one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 may include a plurality of processing units. These processing units may be physically located within the same device (e.g., pressure generator 14), or processor 110 may represent processing functionality of a plurality of devices operating in coordination. For example, in one embodiment, some of the functionality attributed below to processor 110 is divided between a first processor that is operatively connected to a monitor in a device designed to be portable, or even wearable, by a user, and a second processor that communicates with the portable device at least periodically to obtain information, e.g., operational settings, that may be set by the user and further process and/or use the obtained information.

In this embodiment, the second processor of processor 110 may include a processor provided by a host computer. Processors external to other components within system 100 (e.g., the second processor mentioned above) may, in some cases, provide redundant processing to the processors that are integrated with components in system 100 (e.g., the first processor mentioned above), and/or the external processor(s) may provide additional processing to determine additional information related to the operation of system 100.

As is shown in FIG. 1, processor 110 may be configured to execute one or more computer program modules. The one or more computer program modules may include one or more of a control module 111, an indication timing module 112, an interface module 113, a transition timing module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 1 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. As another example, processor 110 may be configured to execute one or more additional modules that may perform some or all of the functionality attributed below to one of modules 111, 112, 113, and/or 114.

Control module 111 may be configured to control pressure generator 14 such that pressure at the airway of the subject prior to a transition time is at a first pressure level, and such that subsequent to the transition time the pressure at the airway of the subject is reduced to a second pressure level that is lower then the first pressure level. The transition time may be determined by transition timing module 114, and/or other components of system 100. Operation of control module 111 may be based on configured settings and/or received commands from the user via user interface 18, settings determined in other components of system 100, and/or other information. The first pressure level may be a positive pressure level. The second pressure level may be a negative pressure level.

Transition timing module 114 may be configured to determine the timing characteristics of the transition time used by control module 111. Timing characteristics of the transition time, such as begin time, duration, and end time, may be shared with or made available to other components of system 100 to aid system operation. For example, transition timing module 114 may cooperate with indication timing module 112 to coordinate the relative timing of the beginning of the transition time and the indicator time.

Indication timing module 112 may be configured to determine an indicator time prior to the transition time at which an indication should be conveyed to the user to initiate treatment to aid airway clearance of the subject, e.g. by compressing the stomach area. Indications may be sensor stimulus indicating that one or more actions should be taken, that one or more events have occurred (or will occur), and/or indicating other information. Indications may include one or more of an auditory indication, a visual indication, a tactile indication, and/or other indications. Indications may include a sequence of multiple auditory indications, visual indications, tactile indications, and/or other indications. An auditory indication may be an audible sound. A visual indication may be a flashing light. A tactile indication may be a vibration.

Interface module 113 may be configured to control user interface 18 to convey information to the user at the indicator time determined by indication timing module 112, e.g. the indication that a user should initiate treatment to aid airway clearance of the subject. Conveying information may include controlling user interface 18 to present and/or display any information—such as an indication—to a user. Alternatively, and/or simultaneously, interface module 113 may be configured to receive user commands and/or feedback that affect operation of one or more computer program modules and/or components in system 100.

Typically, to aid airway clearance a user compresses the stomach area of the subject. At least some of the indications given by system 100 indicate that the user should compress the stomach area of the subject. It will be appreciated that this is not intended to be limiting. The scope of this disclosure extends to any other technique for aiding airway clearance. For example, instead of compressing the stomach, the user may perform an abdominal thrust, and/or may aid airway clearance through other techniques. References in this disclosure to compression of the stomach area are to be understood as shorthand for any of these techniques. System 100 may receive feedback, e.g. via user interface 18, that conveys the delay in the response of the user to the indication. In other words, the feedback includes a measure of past responsiveness of the user. By adjusting the indicator time of a subsequent cycle of insufflation/exsufflation based on this delay, subsequent user-induced and/or manually induced exsufflation may be better synchronized with the mechanical exsufflation performed by system 100.

Alternatively, and/or simultaneously, system 100 may analyze the expiratory airflow of a subject in response to a combination of mechanical and user-induced or manually induced exsufflation, and extract characteristics of the airflow. Characteristics may include peak flow rate, minimum flow rate, transition time from peak to minimum flow rate, shape of the flow rate curve, target flow rate range, duration of airflow at target flow rate range, and/or other characteristics of the expiratory airflow of the subject. Based on characteristics of past expiratory airflows, the indicator time may be automatically adjusted, relative to the transition time, for subsequent mechanical exsufflations performed by system 100. By adjusting the indicator time of a subsequent cycle of insufflation/exsufflation, subsequent user-induced and/or manually induced exsufflation may be better synchronized with the mechanical exsufflation performed by system 100.

Figure 2:
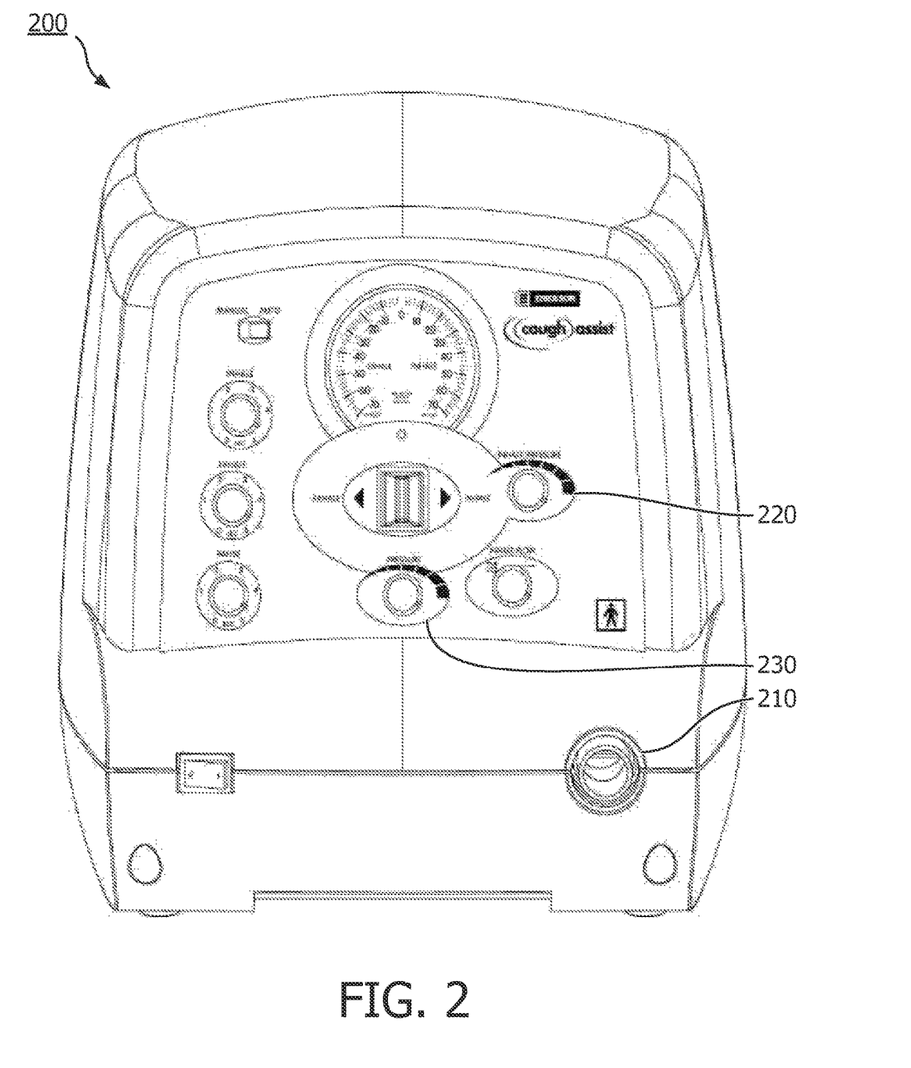
FIG. 2 illustrates an exemplary implementation of an exsufflation system.

FIG. 2 illustrates an exemplary implementation of an exsufflation system 200. System 200 may include subject interface 210, inhale pressure control 220, and pressure control 230. Subject interface 210 may be used to communicate a pressurized flow of breathable gas from a pressure generator to the airway of a subject, and may thus be similar to subject interface 170 in FIG. 1. Inhale pressure control 220 and/or pressure control 230 may be part(s) of the user interface of system 200, used by a user to configure system 200 in accordance with a therapeutic respiratory regimen. Other characteristics of the insufflation/exsufflation cycle, such as inhale duration, exhale duration, and pause between subsequent insufflation/exsufflation cycles, may also be configured through the user interface of system 200.

Figure 3:
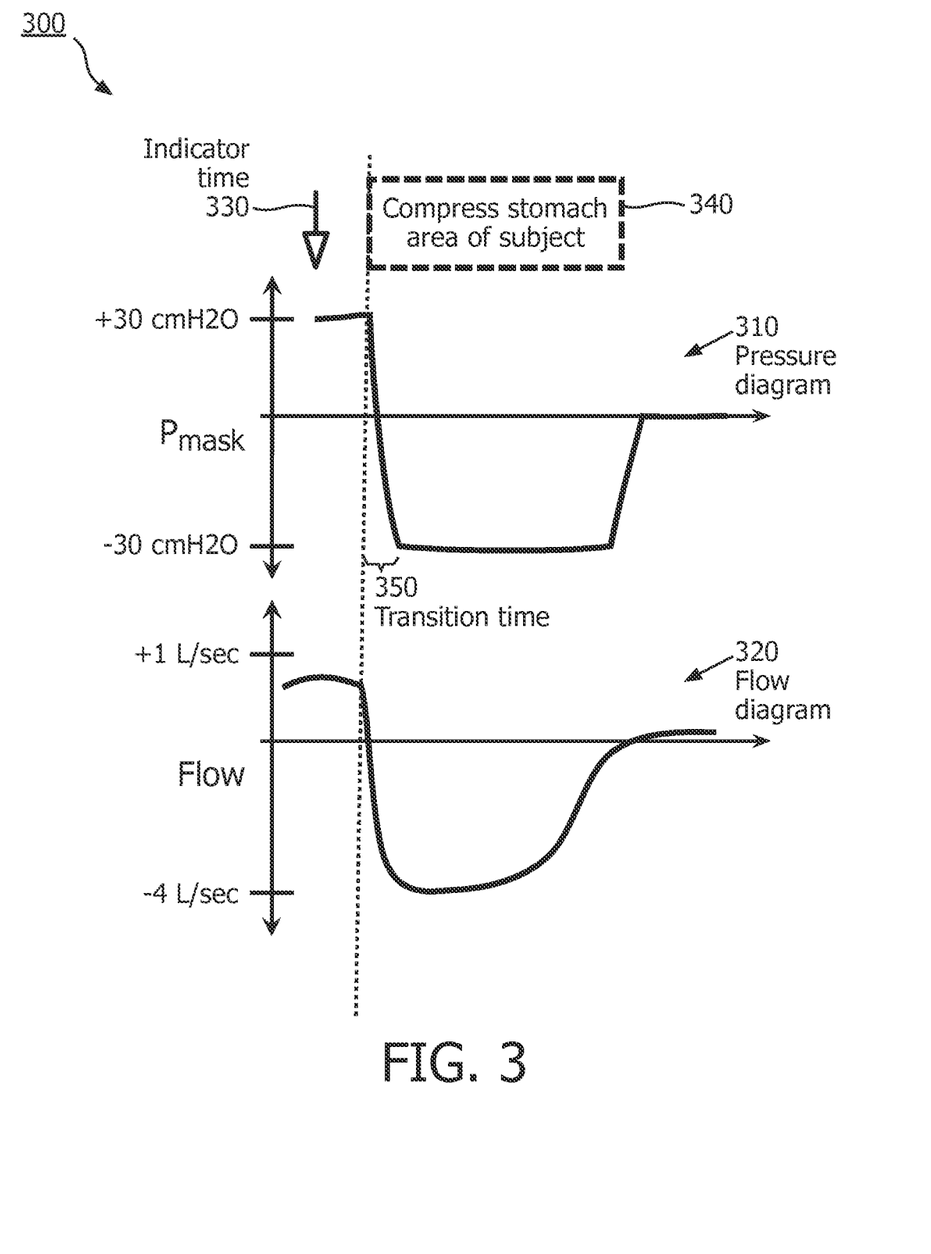
FIG. 3 illustrates a pressure/airflow diagram for a subject undergoing airway pressure therapy.

FIG. 3 illustrates a pressure/airflow diagram 300 for a subject undergoing airway pressure therapy using exsufflation synchronization system 100 of FIG. 1. Diagram 300 includes pressure diagram 310 and flow diagram 320. Pressure diagram 310 illustrates "Pmask" on the y-axis, where "Pmask" represents the pressure measured at the subject interface, e.g. subject interface 170 in FIG. 1. If the subject has a tracheal or endotracheal interface, then "Pmask" represents the pressure measured at that interface. The x-axes of pressure diagram 310 and flow diagram 320 both show time. At indicator time 330, system 100 conveys the indication to the user that the user should initiate treatment to aid airway clearance, e.g. compress the stomach area of the subject. During the time period represented by the width of box 340 in FIG. 3, the user compresses the stomach area of the subject in response to the indication conveyed at indicator time 330. Transition time 350 represents the shortest duration from the first pressure level to the reduced second pressure level. Flow diagram 320 illustrates "Flow" on the y-axis, where "Flow" represents the flow rate, e.g. corresponding to a quantity of liters per second, measured at the subject interface, e.g. subject interface 170 in FIG. 1. If the subject has a tracheal or endotracheal interface, then "Flow" represents the flow rate measured at that interface.

Depending on the specifics of a subject and/or his/her therapy, a user may determine a target flow rate range that is considered optimal for airway clearance. There is a limit to the negative pressure that the airway of a subject can sustain, and that the subject is willing to tolerate. If the compression of the stomach of the subject is properly synchronized with the mechanical exsufflation that occurs after the transition time, as it is for pressure/airflow diagram 300, the flow diagram will show a smooth flow rate curve having the largest possible duration of expiratory airflow at a flow rate within the target flow rate range, in accordance with the therapeutic respiratory regimen of the subject.

Figure 4A:
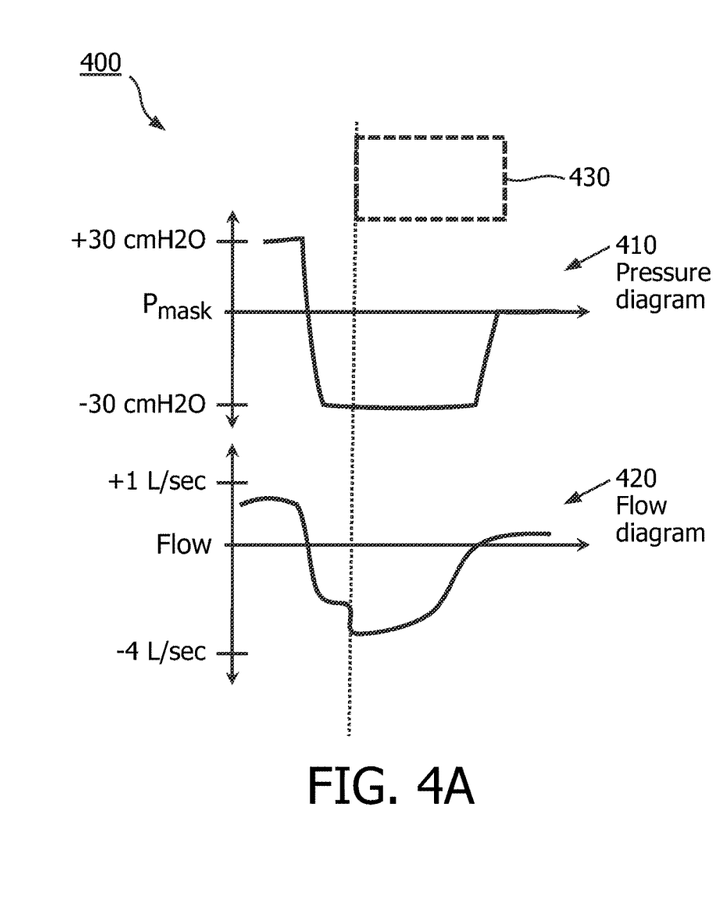
FIG. 4A illustrates a pressure/airflow diagram for a subject undergoing airway pressure therapy with poorly synchronized manually-induced exsufflation.

FIG. 4A illustrates a pressure/airflow diagram 400 for a subject undergoing airway pressure therapy with poorly synchronized manually-induced exsufflation. Diagram 400 includes pressure diagram 410 and flow diagram 420. The units of pressure and flow rate are similar to those in FIG. 3. The user compresses the stomach area of the subject during the time period represented by the width of box 430 in FIG. 4A, but the timing is not properly synchronized—it is late—with the mechanical exsufflation induced by the transition in the airway pressure level of the subject. As a result, flow diagram 420 fails to show a smooth flow rate curve, and fails to have the largest possible duration of expiratory airflow at a flow rate within the target flow rate range.

Figure 4B:
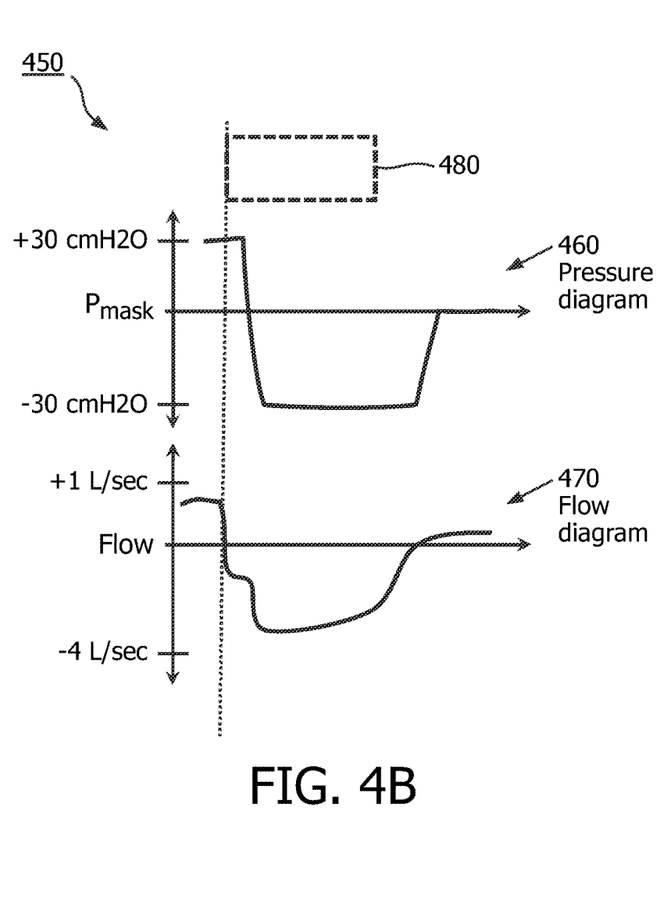
FIG. 4B illustrates a pressure/airflow diagram for a subject undergoing airway pressure therapy with poorly synchronized manually-induced exsufflation.

FIG. 4B illustrates a pressure/airflow diagram for a subject undergoing airway pressure therapy with poorly synchronized manually-induced exsufflation. Diagram 450 includes pressure diagram 460 and flow diagram 470. The units of pressure and flow rate are similar to those in FIG. 3. The user compresses the stomach area of the subject during the time period represented by the width of box 480 in FIG. 4B, but the timing is not properly synchronized—it is early—with the mechanical exsufflation induced by the transition in the airway pressure level of the subject. As a result, flow diagram 470 fails to show a smooth flow rate curve, and fails to have the largest possible duration of expiratory airflow at a flow rate within the target flow rate range.

Figure 5:
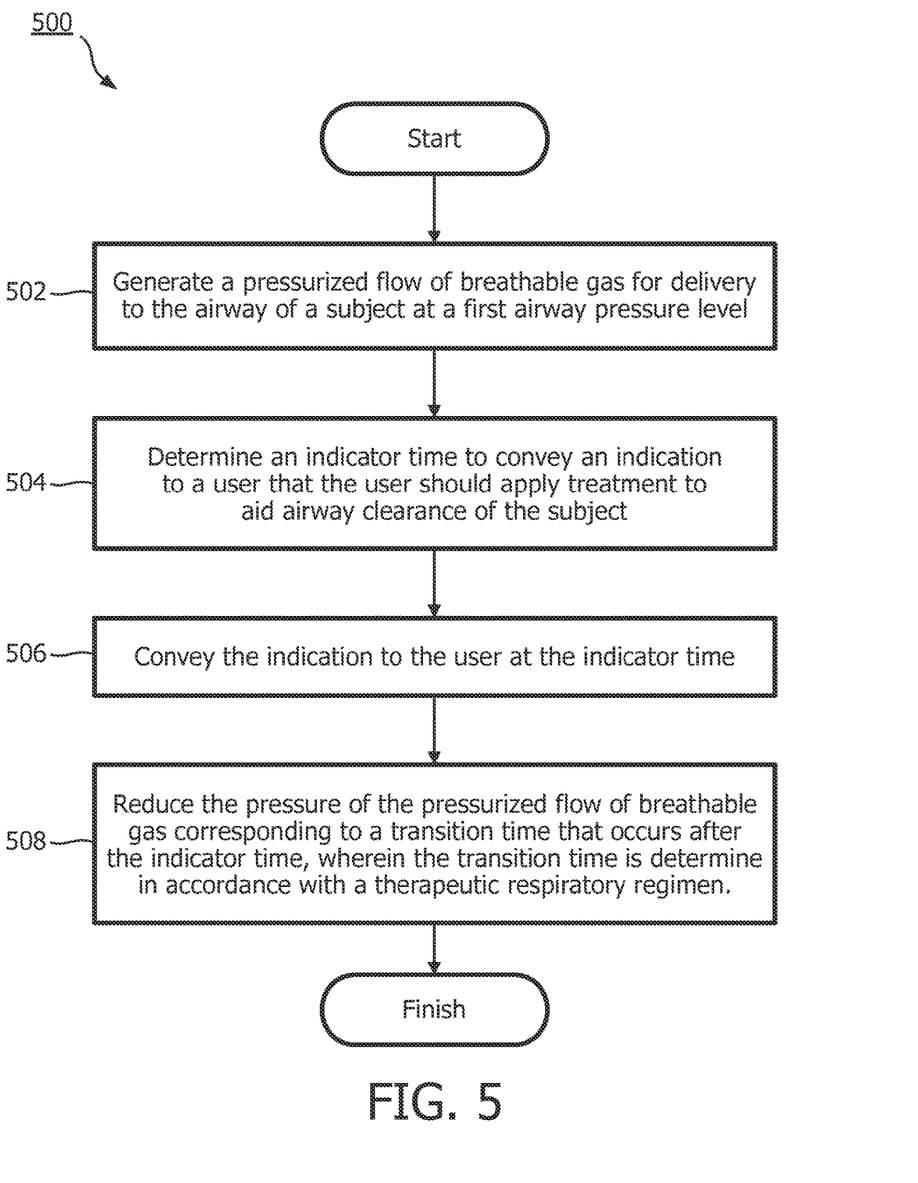
FIG. 5 illustrates an exemplary method for synchronizing exsufflation of a subject, in accordance with one or more embodiments of the present invention.

FIG. 5 illustrates an exemplary method 500 for synchronizing exsufflation of a subject, in accordance with one or more embodiments of the present invention. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium, e.g. an electronic storage medium substantially similar to or the same as electronic storage 16 in FIG. 1. The one or more processing devices may include one or more devices configured through hardware, firmware, and/or software to be specifically designed for execution of one or more of the operations of method 500.

At an operation 502, a pressurized flow of breathable gas is generated for delivery to the airway of a subject at a first airway pressure level. In one embodiment, operation 502 is performed by a pressure generator substantially similar to or the same as pressure generator 14 (shown in FIG. 1 and described above) cooperating with a control module substantially similar to or the same as control module 111 (shown in FIG. 1 and described above).

At an operation 504, an indicator time is determined to convey an indication to a user that the user should initiate treatment to aid airway clearance, e.g. by compressing the stomach area of the subject. In one embodiment, operation 504 is performed by an indication timing module substantially similar to or the same as indication timing module 112 (shown in FIG. 1 and described above) cooperating with a control module substantially similar to or the same as control module 111 (shown in FIG. 1 and described above).

At an operation 506, an indication is conveyed to a user at the indicator time. In one embodiment, operation 506 is performed by an user interface module substantially similar to or the same as user interface module 113 (shown in FIG. 1 and described above) cooperating with a control module substantially similar to or the same as control module 111 (shown in FIG. 1 and described above) and a user interface substantially similar to or the same as user interface 18 (shown in FIG. 1 and described above).

At an operation 508, the pressure of the pressurized flow of breathable gas is reduced to a second pressure level corresponding to a transition time that occurs after the indicator time, wherein the transition time is determined in accordance with a therapeutic regimen. In one embodiment, operation 508 is performed by an pressure generator substantially similar to or the same as pressure generator 14 (shown in FIG. 1 and described above) under control of a control module substantially similar to or the same as control module 111 (shown in FIG. 1 and described above), and in cooperation with a transition timing module substantially similar to or the same as transition timing module 114 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for synchronizing machine-induced expiratory airflow of a subject with user-induced expiratory airflow of the subject, the subject having an airway, the method comprising:
   generating a pressurized flow of breathable gas with a pressure generator for delivery to the airway of the subject at a first pressure level;
   determining, with a processor, an indicator time at which an indication should be conveyed to a user indicating that the user should initiate treatment to aid airway clearance of the subject, wherein the indicator time is determined based on airflow characteristics of the subject, and wherein the indicator time is configured to positively influence an amount of time an expiratory airflow rate of the subject is maintained in a target airflow rate range, the airflow characteristics of the subject including one or more of, minimum flow rate, transition time from peak to minimum flow rate, shape of a flow rate curve, or a duration of airflow at a target flow rate range;
   determining with the processor, a transition time, the transition time indicative of a time from a maximum flow rate to a minimum flow rate of the subject, wherein the indicator time commences prior to the transition time;
   controlling the pressure generator with the processor such that the pressurized flow of breathable gas at the airway of the subject prior to the start of the transition time is at a first pressure level, and such that subsequent to the end of the transition time the pressurized flow of breathable gas at the airway of the subject is at a second pressure level that is lower than the first pressure level; and
   providing, via a user interface, the indication to the user at the indicator time, wherein the indication is conveyed to the user to initiate the treatment while the pressurized flow of breathable gas at the airway of the subject is at the second pressure level.

2. The method of claim 1, wherein the indication includes one or more of an auditory indication, a visual indication, or a tactile indication.

3. The method of claim 1, further comprising determining the indicator time based on past responsiveness of the user to indications that the user should initiate treatment to aid airway clearance of the subject.

4. The method of claim 1, further comprising determining the indicator time based on characteristics of past expiratory airflows of the subject corresponding to past transition times.

5. The method of claim 1, wherein the treatment to aid airway clearance of the subject comprises manual compression of the stomach area of the subject.

6. A system for synchronizing machine-induced expiratory airflow of a subject with user-induced expiratory airflow of the subject, the subject having an airway, the system comprising:
   a pressure generator configured to generate a pressurized flow of breathable gas for delivery to the airway of the subject; and
   one or more processors configured by machine-readable instructions to:
      determine an indicator time at which an indication is conveyed to a user to initiate treatment to aid airway clearance of the subject, wherein the indicator time is determined based on airflow characteristics of the subject, and wherein the indicator time is configured to positively influence and amount of time an expiratory airflow rate of the subject is maintained in a target airflow rate range, the airflow characteristics of the subject including one or more of, minimum flow rate, transition time from peak to minimum flow rate, shape of a flow rate curve, or a duration of airflow at a target flow rate range;
      determine a transition time, the transition time indicative of a time from a maximum flow rate to a minimum flow rate of the subject, wherein the indicator time commences prior to the transition time;
      control the pressure generator such that the pressurized flow of breathable gas at the airway of the subject prior to the start of the transition time is at a first pressure level, and such that subsequent to the end of the transition time the pressurized flow of breathable gas at the airway of the subject is at a second pressure level that is lower than the first pressure level; and
      provide, via a user interface, the indication to the user at the indicator time, wherein the indication is conveyed to the user to initiate the treatment while the pressurized flow of breathable gas at the airway of the subject is at the second pressure level.

7. The system of claim 6, wherein the one or more processors are configured such that the indication includes one or more of an auditory indication, a visual indication, or a tactile indication.

8. The system of claim 6, wherein the one or more processors are further configured such that the indicator time is determined based on past responsiveness of the user to indications that the user should initiate treatment to aid airway clearance of the subject.

9. The system of claim 6, wherein the one or more processors are further configured such that the indicator time is determined based on characteristics of past expiratory airflows of the subject corresponding to past transition times.

10. The system of claim 6, wherein the treatment to aid airway clearance of the subject comprises manual compression of the stomach area of the subject.

11. A system configured to synchronize machine-induced expiratory airflow of a subject with user-induced expiratory airflow of the subject, the subject having an airway, the system comprising:

means for generating a pressurized flow of breathable gas for delivery to the airway of the subject at a first pressure level;

means for determining an indicator time at which an indication should be conveyed to a user indicating that the user should initiate treatment to aid airway clearance of the subject, wherein the indicator time is determined based on airflow characteristics of the subject, and wherein the indicator time is configured to positively influence an amount of time an expiratory airflow rate of the subject is maintained in a target airflow rate range, the airflow characteristics of the subject including one or more of, minimum flow rate, transition time from peak to minimum flow rate, shape of a flow rate curve, or a duration of airflow at a target flow rate range;

means for determining a transition time, the transition time indicative of a time from a maximum flow rate to a minimum flow rate of the subject, wherein the indicator time commences prior to the transition time;

means for controlling the pressure generator such that the pressurized flow of breathable gas at the airway of the subject prior to the start of the transition time is at a first pressure level, and such that subsequent to the end of the transition time the pressurized flow of breathable gas at the airway of the subject is a at a second pressure level that is lower than the first pressure level; and means for providing the indication to the user at the indicator time, wherein the indication is conveyed to the user to initiate the treatment while the pressurized flow of breathable gas at the airway of the subject is at the second pressure level.

12. The system of claim 11, wherein the indication includes one or more of an auditory indication, a visual indication, or a tactile indication.

13. The system of claim 11, wherein the operation of the means for determining the indicator time is further based on past responsiveness of the user to indications that the user should initiate treatment to aid airway clearance of the subject.

14. The system of claim 11, wherein the operation of the means for determining an indicator time is further based on characteristics of past expiratory airflows of the subject corresponding to past transition times.

15. The system of claim 11, wherein the treatment to aid airway clearance of the subject comprises manual compression of the stomach area of the subject.

* * * * *